Figure 1:
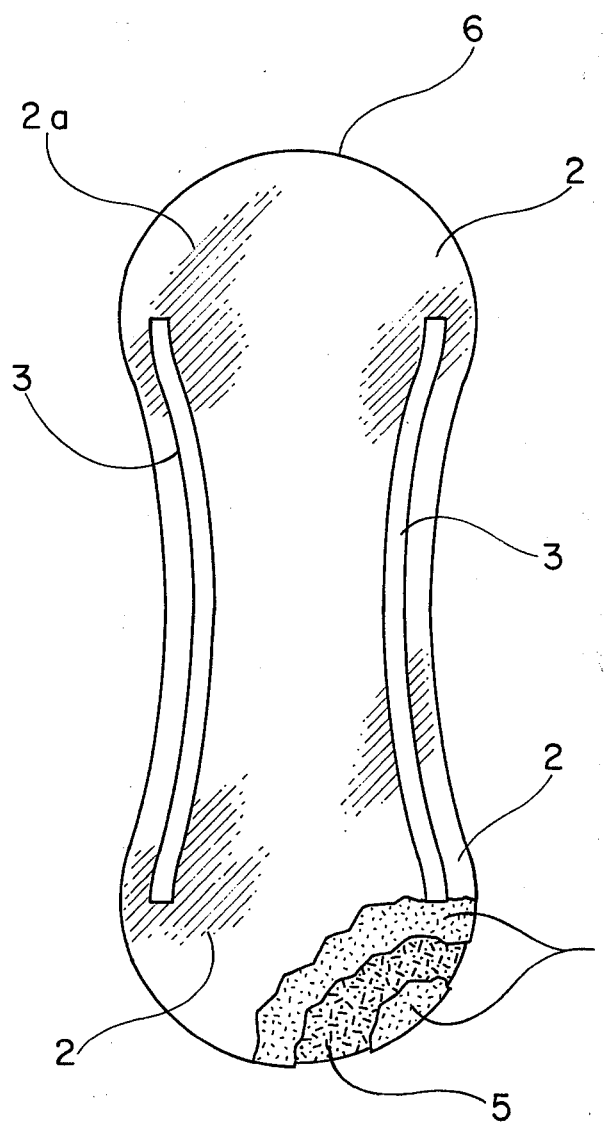

United States Patent [19]

Matthews

[11] 4,333,466
[45] Jun. 8, 1982

[54] SANITARY NAPKIN WITH IMPROVED PANTY ADHESIVE

[75] Inventor: Billie J. Matthews, Menasha, Wis.

[73] Assignee: Kimberly-Clark Corporation, Neenah, Wis.

[21] Appl. No.: 175,298

[22] Filed: Aug. 5, 1980

[51] Int. Cl.³ .............................................. A61F 13/16
[52] U.S. Cl. ....................... 128/290 R; 128/DIG. 30
[58] Field of Search ............ 128/287, 290 R, DIG. 30

[56] References Cited

U.S. PATENT DOCUMENTS

| | | | |
|---|---|---|---|
| 3,454,008 | 8/1969 | Hendricks | 128/290 R |
| 3,688,771 | 9/1972 | Werner | 128/290 R |
| 4,059,114 | 11/1977 | Richards | 128/287 |

Primary Examiner—C. Fred Rosenbaum
Attorney, Agent, or Firm—Howard Olevsky; William D. Herrick

[57] ABSTRACT

A sanitary napkin having body-shape conforming inwardly arcuate recesses along its longitudinal axis is provided. The napkin has pressure sensitive adhesive means equidistantly recessed along each inwardly arcuate edge.

5 Claims, 1 Drawing Figure

U.S. Patent  Jun. 8, 1982  4,333,466

SANITARY NAPKIN WITH IMPROVED PANTY ADHESIVE

BACKGROUND OF THE INVENTION

Sanitary napkins having pressure sensitive adhesive means for attachment of the napkin to a supporting undergarment have received substantial consumer acceptance over the past several years. These napkins are generally characterized by parallel longitudinal sides and extending tab areas at each end thereof.

These napkins typically have an absorbent pad, a fluid permeable cover and a fluid impermeable baffle. The baffle may be attached adhesively or it may be fused to the wrap or to the absorbent pad itself. The pressure sensitive adhesive utilized for garment attachment is applied either directly to the baffle or, if the outer wrap encircles the baffle it may be applied to that component and, as taught in U.S. Pat. No. 3,674,595 may actually serve to adhere the wrap to the baffle and attach the overlapping ends of the wrap.

Regardless of whether the adhesive is applied to the wrap or to the baffle, the particular placement of the adhesive along the undergarment-facing side of the pad determines to a large extent, both the effectiveness of the adhesive attachment and the comfort of the napkin to the user when the user is active.

A variety of configurations for adhesive placement have been taught in the past, see for example, U.S. Pat. No. 3,454,008 which describes adhesive placement at the ends of the napkin and U.S. Pat No. 3,674,595 which discloses a napkin having adhesive lines parallel to but recessed slightly inward from the longitudinal margins of the napkin. This slightly inwardly recessed configuration which is parallel to the longitudinal edges, has achieved wide consumer acceptance as being extremely effective in maintaining the attachment of the napkin to the undergarment.

Recently, however, sanitary napkins have been introduced which have inwardly arcuate edges along each of the longitudinal sides. This configuration conforms to a greater degree to the geometry of the perineal area and, as a result, is more comfortable for the wearer. Sanitary napkins with these inwardly arcuate configurations are generally of the so-called panty liner type. These napkins are designed to be substantially less bulky and are specifically adapted for use either with a tampon or for days when there is only light menstrual flow or other slight vaginal discharge.

The panty liner type of sanitary napkin, because of its reduced bulk, has increased flexibility and is much more likely to contort during activity by the wearer. Where napkins of this configuration are attached by twin adhesive lines parallel to each other, there is a substantial variance in the distance between the edge of the napkin at the center of the arc and at the ends of the cutout area. The distance between the adhesive lines and the ends of the cutout area is substantially greater than that at the deepest inward portion of the arc and, during normal use, this free, unattached portion of the napkin may be folded back onto itself at the bottom and actually adhere to the adhesive designed for attachment to the undergarment at each end of the panty liner. In addition, the non-adhered free ends at the napkin edges may produce substantial chafing due to the flexibility and freedom of movement in these locations.

SUMMARY OF THE INVENTION

According to this invention a sanitary napkin having arcuate body-shaped conforming contours along the longitudinal edges thereof is provided with pressure sensitive adhesive strips for attachment to undergarments, with these strips being equidistant from the inwardly arcuate edges of the sanitary napkin.

In one particularly preferred embodiment, a panty liner having the configurational characteristics described above is provided with these contoured adhesive lines.

For purposes of this invention, a panty liner is defined as a sanitary napkin having an absorbent component and a fluid impervious baffle and having an overall thickness of less than $\frac{3}{8}$". The panty liner may optionally have a fluid pervious wrap.

The invention may be more readily understood by reference to the drawings in which FIG. 1 is a bottom plan view partially in cross section of a napkin embodying the teachings of this invention.

As can be seen from FIG. 1, a sanitary napkin having a baffle 2 with a flexible undergarment facing surface 2a is provided with a pair of adhesive lines 3. The sanitary napkin has a fluid pervious cover wrap 4 which encircles the absorbent pad 5 and is attached to the baffle 2 at its upper surface. The napkin has outwardly arcuate curvilinear surface 6 at the ends thereof and a pair of inwardly arcuate edges 7 along the longitudinal sides thereof. As can be seen from FIG. 1, the adhesive lines 3 extend essentially uniformly inward from the longitudinal sides in equal spaced relationship.

Although the distance between the outward edge of the adhesive line and the longitudinal edge of the sanitary napkin may vary depending upon the size of the napkin and the stiffness of the baffle among other factors, it is generally preferred that this distance be at least $\frac{1}{4}$". Obviously, the more flexible the baffle is the greater the danger for engagement of the baffle itself with the adhesive lines and with highly flexible baffles, it is preferred that the adhesive be closer to the longitudinal edges of the napkin.

It is preferred that the adhesive strips terminate at either end before the outward curvature of the ends 6 begins. This is true because it is difficult to control the distance placement as the curve of the napkin is directed outwardly and, also, it has been found that adhesive at the ends of the napkin 6 may end up attached to the wearer rather than the undergarment. This is particularly true where the ends are designed to be tab ends, i.e. where no absorbent media is present at the ends of the napkin. This increasing flexibility enhances the possibility for this unwanted adhesive attachment.

What is claimed is:

1. A sanitary napkin comprising an absorbent layer and a fluid impervious baffle, attached thereto said napkin having inwardly arcuate edges along the sides of said baffle and a plurality of pressure sensitive adhesive strips corresponding to each of these edges, said adhesive strips each being spaced equidistantly from the longitudinal edges in the arcuate portion of the napkin.

2. The sanitary napkin according to claim 1 wherein the ends of the napkin are outwardly arcuate.

3. A sanitary napkin according to claims 1 or 2 wherein the adhesive strips terminate before the outwardly arcuate portion of the ends.

4. A panty liner comprising an absorbent layer and a fluid impervious baffle attached thereto, said napkin having inwardly arcuate edges along the sides of said baffle and a plurality of pressure sensitive adhesive strips corresponding to each of these edges, said adhesive strips corresponding to each of these edges, said adhesive strips each being spaced equidistantly from the longitudinal edges in the arcuate portion of the panty liner.

5. A sanitary napkin according to claims 1, 2, 3 or 4 in which the distance between the adhesive and the outer edge is at least $\frac{1}{4}''$.

* * * * *